United States Patent
Isenhart et al.

(10) Patent No.: US 9,089,310 B2
(45) Date of Patent: *Jul. 28, 2015

(54) METHOD AND DEVICE FOR REMOVING EEG ARTIFACTS

(71) Applicants: Brainscope Company, Inc., Bethesda, MD (US); New York University, New York, NY (US)

(72) Inventors: Robert Isenhart, Brooklyn, MA (US); Arnaud Jacquin, New York, NY (US); Leslie Prichep, Mamaroneck, NY (US)

(73) Assignee: BrainScope Company, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/751,448

(22) Filed: Jan. 28, 2013

(65) Prior Publication Data

US 2013/0211224 A1 Aug. 15, 2013

Related U.S. Application Data

(63) Continuation of application No. 12/720,861, filed on Mar. 10, 2010, now Pat. No. 8,364,255.

(51) Int. Cl.
*A61B 5/04* (2006.01)
*A61B 5/00* (2006.01)
*A61B 5/0476* (2006.01)
*A61B 5/0478* (2006.01)

(52) U.S. Cl.
CPC ........... *A61B 5/7207* (2013.01); *A61B 5/04012* (2013.01); *A61B 5/0476* (2013.01); *A61B 5/0478* (2013.01); *A61B 5/6831* (2013.01)

(58) Field of Classification Search
USPC ................................... 600/544, 545
See application file for complete search history.

(56) References Cited

U.S. PATENT DOCUMENTS

| | | | |
|---|---|---|---|
| 4,279,258 | A | 7/1981 | John |
| 4,564,022 | A | 1/1986 | Rosenfeld et al. |
| 5,467,777 | A | 11/1995 | Farwell |
| 6,067,467 | A | 5/2000 | John |
| 6,589,189 | B2 | 7/2003 | Meyerson et al. |
| 2004/0010203 | A1 | 1/2004 | Bibian et al. |
| 2007/0106169 | A1 | 5/2007 | Fadem |
| 2007/0255164 | A1 | 11/2007 | Viertio-oJa et al. |
| 2007/0299359 | A1 | 12/2007 | Olsson et al. |
| 2008/0097235 | A1* | 4/2008 | Ofek et al. ............ 600/544 |
| 2008/0208073 | A1 | 8/2008 | Causevic |
| 2010/0041962 | A1 | 2/2010 | Causevic et al. |
| 2011/0182143 | A1* | 7/2011 | Liu et al. ............ 367/47 |

OTHER PUBLICATIONS

Anderer et al., "Artifact Processing in Computerized Analysis of Sleep EEG—A Review," Neuropsychobiology, vol. 40, pp. 150-157, 1999.

Claassen et al., "Continuous Electroencephalographic Monitoring in Neurocritical Care," Current Neurology and Neuroscience Reports, vol. 2, pp. 534-540, 2002.

(Continued)

*Primary Examiner* — Etsub Berhanu
(74) *Attorney, Agent, or Firm* — Finnegan, Henderson, Farabow, Garrett & Dunner, LLP (57) ABSTRACT

Systems and methods for automatically identifying segments of EEG signals or other brain electrical activity signals that contain artifacts, and/or editing the signals to remove segments that include artifacts.

7 Claims, 10 Drawing Sheets

(56) References Cited

OTHER PUBLICATIONS

Durka et al., "A Simple System for Detection of EEG Artifacts in Polysomnographic Recordings," IEEE Transactions on Biomedical Engineering, vol. 50, No. 4, pp. 526-528, Apr. 2003.

Gevins et al., "Normative Data Banks and Neurometrics. Basic Concepts, Methods and Results of Norm Constructions," Handbook of Electroencephalography and Clinical Neurophysiology (Revised Series vol. 1), pp. 449-495, 1987.

Guerit, "Medical technology assessment EEG and evoked potentials in the intensive care unit," Neurophysiol Clin., vol. 29, pp. 301-317, 1999.

Hall, "Intensive Care Unit (ICU) Monitoring," Handbook of Auditory Evoked Responses, pp. 534-579, 1992.

Jacquin et al., "Automatic Identification of Spike-Wave Events and Non-Convulsive Seizures with a Reduced Set of Electrodes," Proceedings of the 29th Annual International Conference of the IEEE EMBS, pp. 1928-1932, Aug. 2007.

John et al., "Neurometric Classification of Patients with Different Psychiatric Disorders," In Statistics and Topography in Quantitative EEG, Ed., D. Sampson-Dollfus, pp. 88-95, Paris: Elsevier, 1988.

Jung et al., "Removing electroencephalographic artifacts by blind source separation," Psychophysiology, vol. 37, pp. 163-178, 2000.

Lehnertz et al., "Can Epileptic Seizures be Predicted? Evidence form Nonlinear Time Series Analysis of Brain Electrical Activity," Physical Review Letters, vol. 80, No. 22 pp. 5019-5022, 1998.

MacCrimmon et al., "Computerized Pattern Recognition of EEG Artifact," Brain Topography, Vo. 6, No. 1, pp. 21-25, 1993.

Romero et al., "A comparative study of automatic techniques for ocular artifact reduction in spontaneous EEG signals based on clinical target variables: A simulation case," Computers in Biology and Medicine 38, pp. 348-360, 2008.

Thatcher et al., "An EEG Severity Index of Traumatic Brain Injury," J. Neuropsychiatry Clin Neurosci, vol. 13, No. 1, pp. 77-87, 2001.

U.S. Appl. No. 12/720,907, filed Mar. 10, 2010.

Vespa et al., "Early detection of vasospasm after acute subarachnoid hemorrhage using continuous EEG ICU monitoring," Electroencephalography and clinical Neurophysiology, vol. 103, pp. 607-615, 1997.

Causevic et al., "Fast Wavelet Estimation of Weak Biosignals," Engineering, IEEE Service Center, Piscataway, NJ, vol. 52, No. 6, pp. 1021-1032, 2005.

Jacquin et al., "Adaptive complex wavelet-based filtering of EEG for extraction of evoked potential responses", Proc. IEEE Int. Conf. Acoust., Speech, and Signal Proc., Philadelphia, PA, Mar. 2005, pp. V:393-396.

Jacquin et al., "Optimal denoising of Brainstem Auditory Evoked Response (BAER) for automatic Peak Identification and Brainstem Assessment", Proceedings of the 28th IEEE EMBS Annual Int'l Conference, New York, Aug. 30-Sep. 3, 2006, pp. 1723-1726.

PCT International Search Report and Written Opinion mailed Jun. 17, 2011 in related PCT/US2011/027651.

PCT International Search Report and Written Opinion mailed Jul. 4, 2011, in related PCT/US2011/027525.

\* cited by examiner

METHOD AND DEVICE FOR REMOVING EEG ARTIFACTS

CROSS-REFERENCE TO RELATED APPLICATIONS

This is a continuation of application Ser. No. 12/720,861, filed Mar. 10, 2010, which is incorporated herein by reference.

The present disclosure pertains to devices and methods for collecting brain electrical activity data, and specifically to devices and methods for automatically editing brain electrical activity signals.

Automatic analysis of EEG data or other types of brain electrical activity date using, for example, Quantitative Assessment of EEG, requires signals that are free of noise due to physiologic and non-physiologic factors. Attempts at obtaining artifact-free data have included methods for eliminating artifacts from EEG signals, thereby leaving only the underlying brain electrical activity signal, or by identifying EEG segments that contain artifacts and manually editing EEGs to remove segments affected by artifact.

Current systems and methods for automatically filtering EEG signals have limited accuracy and may not reliably identify and/or remove all artifacts. In addition, manual editing of EEGs is time consuming and subject to user bias. Accordingly, there is a need for improved methods for automatically identifying EEG artifacts and editing EEGs to remove segments affected by artifacts.

A device for automatically editing brain electrical activity data is provided. The device comprises at least two EEG electrodes; a circuit for measuring electrical potential signals from the electrodes; a memory unit configured to store data related to the electrical potential; an analysis unit configured to analyze the signal to determine if temporal segments of the signal include artifacts due to of any of eye movements, cable or electrode movements, impulse artifacts, and muscle activity, and if any segment does include artifacts, identifying the segment as including artifacts; and editing the data in the analysis unit to remove segments that include artifacts.

A method for automatically editing brain electrical activity data is provided. The method comprises positioning at least two frontal EEG electrodes on a patient; obtaining a signal representing brain electrical activity in each of the electrodes; analyzing the signal to determine if temporal segments of the signal include artifacts due to of any of eye movements, cable or electrode movements, impulse artifacts, and muscle activity, and if any segment does include artifacts identifying the segment as including artifacts; and editing the signal to remove segments that include artifacts.

DESCRIPTION OF EXEMPLARY EMBODIMENTS

The present disclosure provides devices and methods for analyzing brain electrical activity, including editing brain electrical activity data to identify and remove brain electrical activity signals that contain certain types of artifacts.

As used herein, "EEG signal" or "signal" refers to recordings of cerebral electrical activity, or other types of brain electrically activity, recorded from any location on the cranium. EEG or other brain electrical activity data can be stored as a digital signal in a memory unit. As used herein, "artifacts" or "noise" refers to any electrical potential recorded while obtaining an EEG or other brain electrical activity signal that is not of cerebral origin or is the result of abnormal brain activity. As used herein, "EEG electrode" refers to any electrode placed on a person's head and capable of detecting brain electrical activity. EEG electrodes can be placed according to known positioning systems, such as, the expanded international 10/20 placement system. In addition, as used throughout, EEG can include cerebral electrical activity or other types of brain electrical activity, and it will be understood that the methods of the present disclosure can be used to identify and remove artifacts from any type of brain electrical activity signal.

Most systems that rely on quantitative analysis of EEG typically assume that a trained technologist has manually edited the raw data to remove artifacts. However, the editing process can be time-consuming and is inherently subjective. In addition, technologist editing prevents automated monitoring, and therefore, is not suitable for continuous and rapid monitoring (e.g., in an ICU, in a field hospital, at a sporting event, or in typical primary care settings). The following processing techniques can be used to automatically identify and/or remove (e.g., edit out) EEG or other brain electrical activity data segments that include artifacts. This may be accomplished using standard signal processing components, which include digital filtering (low-pass filtering, bandpass filtering, etc.), thresholding, peak detection, and frequency-based processing.

There are seven typical types of noise that can contribute to poor signal quality. EEG segments including each of these types of artifacts, as recorded with a limited electrode montage (i.e., 5 electrodes) are shown in FIGS. 3-9, with the segment containing artifact data identified by a dark dashed-line box. These EEGs were recorded with electrode impedances under 5 kΩ. The data was sampled at 8 kHz, low-pass filtered to remove signal frequencies above 45 Hz, and down-sampled to 100 Hz for purposes of display and editing. These artifacts include (1) horizontal/lateral eye movements (HEM) (see FIG. 3, 300), (2) vertical eye movements (e.g. blinks)

Figure 9:
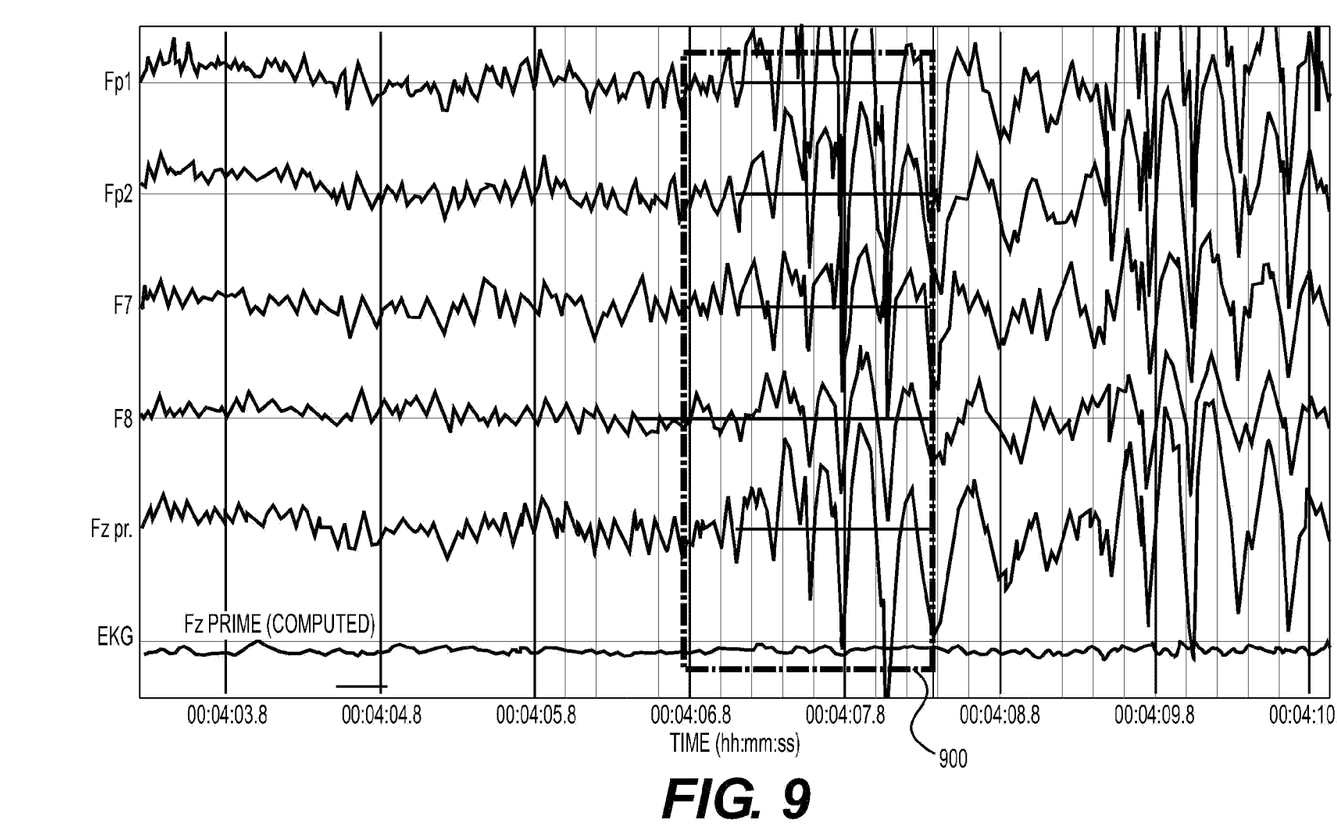
FIG. 9 shows approximately eight seconds of EEG that includes Atypical Electrical Activity Pattern (AEAP).

(VEM) (see FIG. 4, 400), (3) cable or electrode movement causing over-range artifacts (PCM) (see FIG. 5, 500), (4) impulse artifacts (for example due to electrode "pops") (IMP) (see FIG. 6, 600), (5) electromyographic activity (also referred to as "muscle activity") (EMG) (see FIG. 7, 700), (6) significantly low amplitude signal (for example as a result of the suppression component of "burst suppression") (SLAS) (see FIG. 8, 800), and (7) atypical electrical activity pattern (for example due to paroxysmal brain activity) (AEAP) (see FIG. 9, 900). Out of these seven artifact types, two are non-physiological (type 3, type 4), three are physiological, but are not brain-generated (type 1, 2, type 5) and two are brain-generated (type 6, type 7). All of these artifacts reflect either non-brain electrical activity or abnormal brain-electrical activity.

The present disclosure provides a comprehensive, fully-automated, artifact detection system, mimicking the ability of trained EEG technologists to edit EEG records. The edited records may be used for subsequent processing and analysis, using, for example, quantitative analyses of brain electrical activity. In certain embodiments, the method and device of the present disclosure can include a limited frontal electrode montage, as described further below.

In certain embodiments, the present disclosure provides a device and method for automatically editing EEG signals. In certain embodiments, the method comprises positioning at least two frontal EEG electrodes on a patient, and obtaining a signal representing brain electrical activity in each of the electrodes. The signal can be analyzed to determine if temporal segments of the signal include artifacts due to of any of eye movements, cable or electrode movements, impulse artifacts, and muscle activity, and if any segment does include artifacts identifying the segment as including artifacts. In some embodiments, the signal is edited to remove segments that include artifacts. In some embodiments, the method further includes analyzing the signal to determine if temporal segments of the signal include artifacts due to of any significantly low amplitude signal and atypical electrical activity.

Figure 1A:
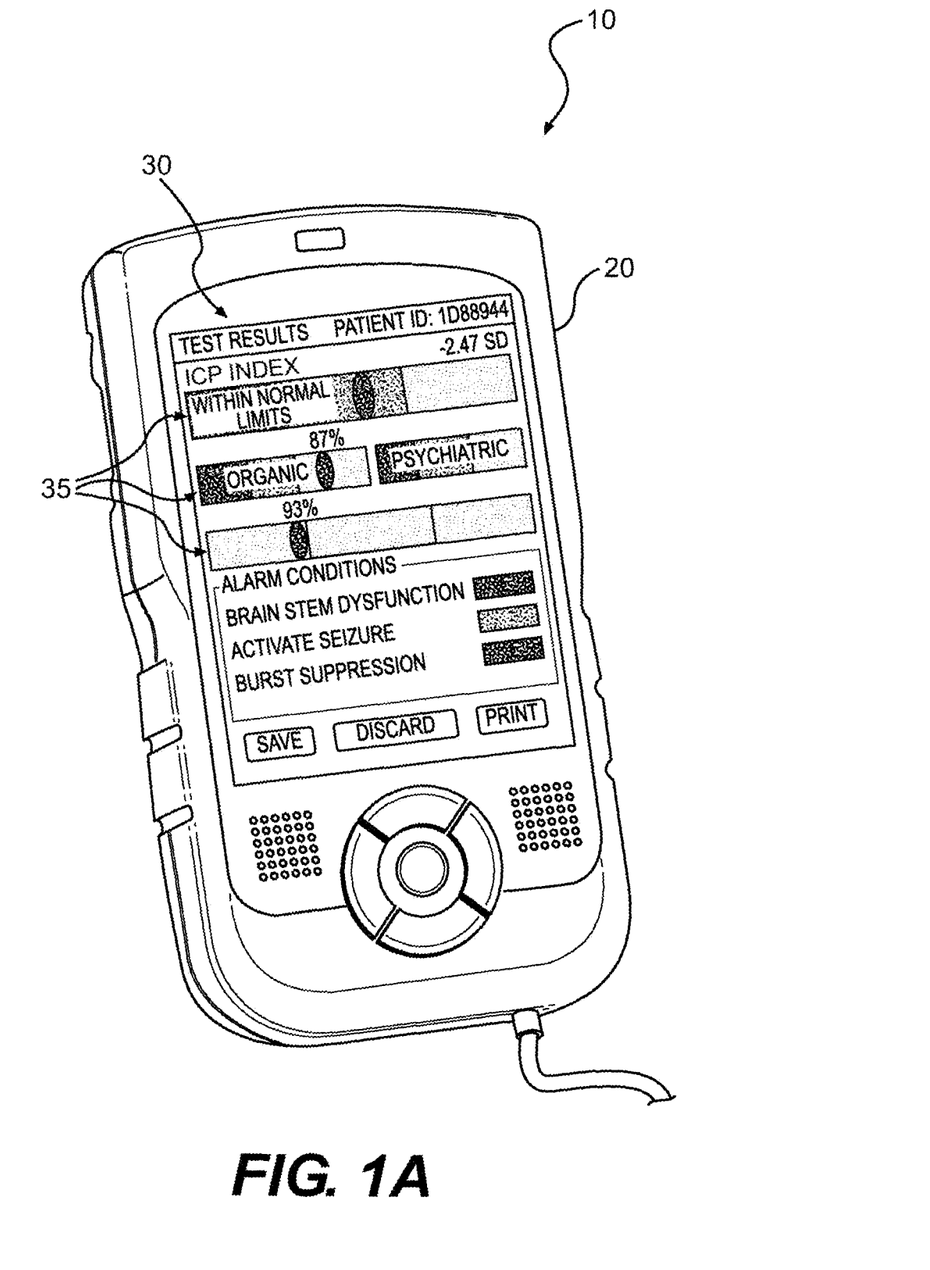
FIG. 1A illustrates a brain electrical activity monitoring system according to one embodiment of the present disclosure.

A number of different EEG systems can be used to collect data using the methods of the present disclosure. In certain embodiments, the system can be a compact, self-contained device. For example, FIG. 1A illustrates an EEG system 10, according to certain embodiments of the present disclosure. As shown, the system 10 can include an enclosure 20 containing electrical circuitry configured to perform data processing, stimulus generation, and analysis for diagnosis and patient monitoring. In addition, the enclosure 20 may further include a display system 30, such as an LCD or other visual display to provide real-time, easy-to-interpret information related to a patient's clinical status.

In some embodiments, the system 10 will include circuitry configured to provide real-time monitoring of brain electrical activity. The system 10 will provide rapid data acquisition, processing, and analysis to allow point-of-care diagnosis and assessment. For example, as shown, the display system 30 can include one or more indicators 35, or visual displays, that are configured to display an easy-to-interpret indication of a patient's status. In one embodiment, the indicators 35 will include an indication of where a patient's status lies relative to a normal data set, a patient's status relative to a base line, and/or one or more indicators of the origin of any abnormalities. In some embodiments, the indicators provide a scale (from normal to severely abnormal). In other embodiments, typical EEGs, as shown in the attached figures may be displayed on the system 30, as recorded and/or after editing.

Figure 1B:
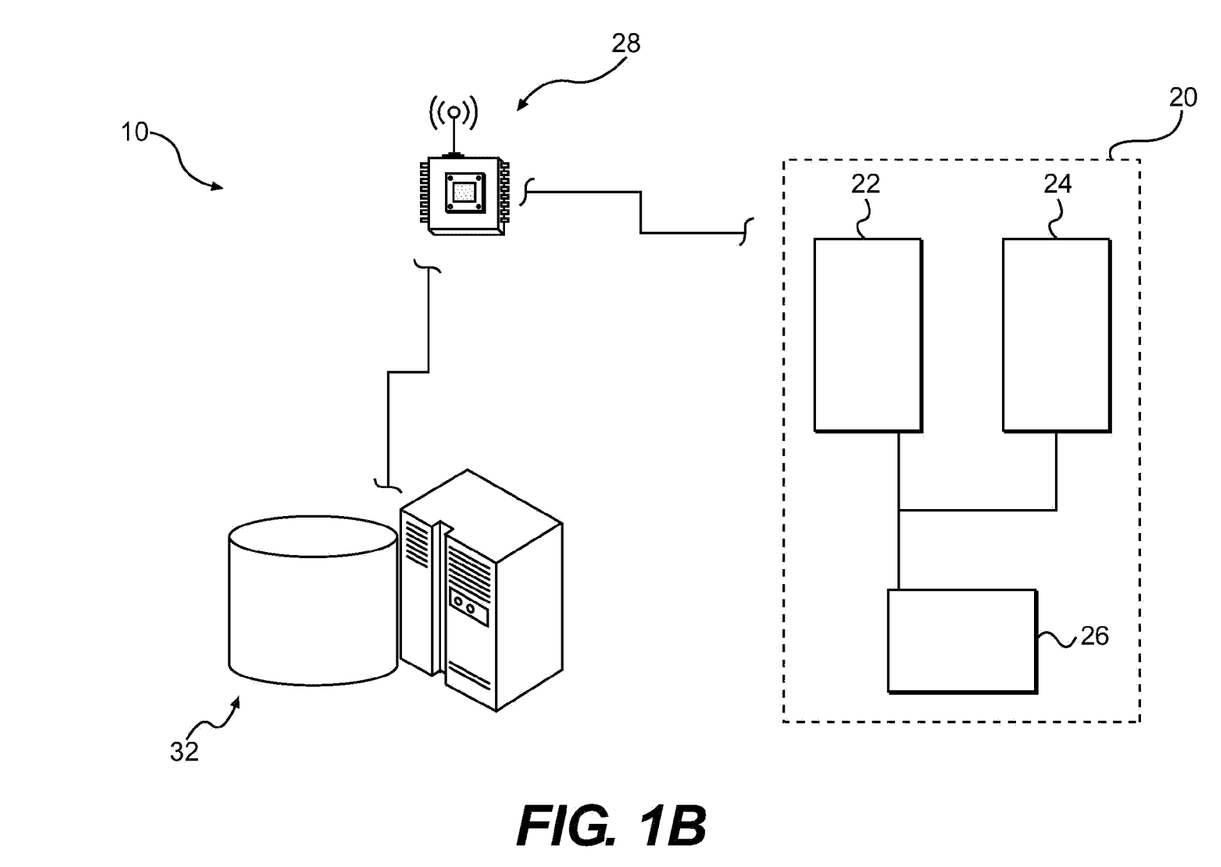
FIG. 1B illustrates a schematic diagram of the monitoring system of FIG. 1A, illustrating additional components.

FIG. 1B illustrates a schematic diagram of the monitoring system of FIG. 1A, illustrating additional components. As shown, the enclosure 20, can include a number of component parts. For example, the enclosure 20 may include a memory unit or storage system 22 configured to store data related to patient brain electrical activity data measurements, or a database of normal and/or pathological readings. Further, the enclosure will include circuitry configured to process and evaluate electrical signals and data 24, and a transmitter unit 26.

Figure 2A:
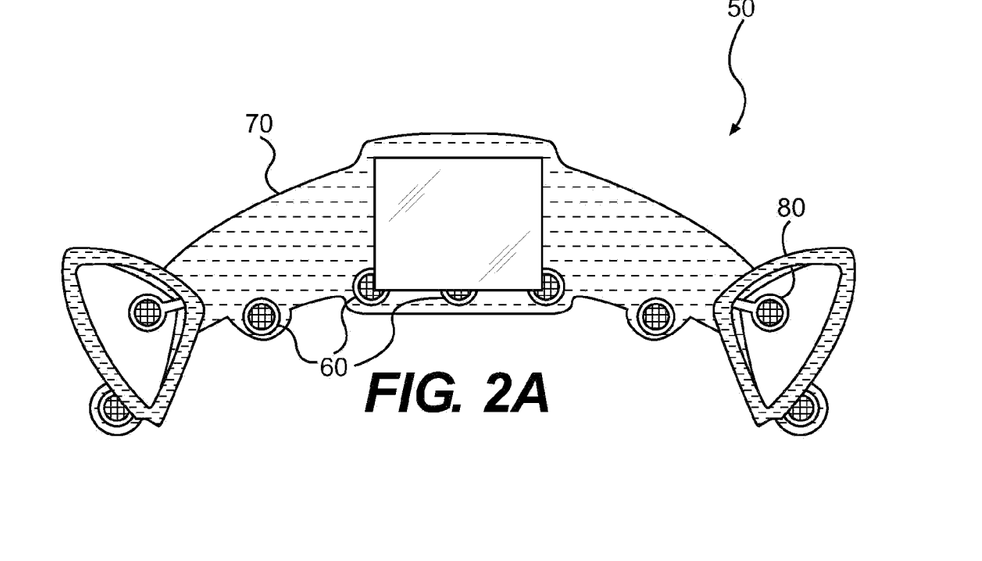
FIG. 2A illustrates an electrode set for use with the brain electrical activity monitoring system of the present disclosure.
Figure 2B:
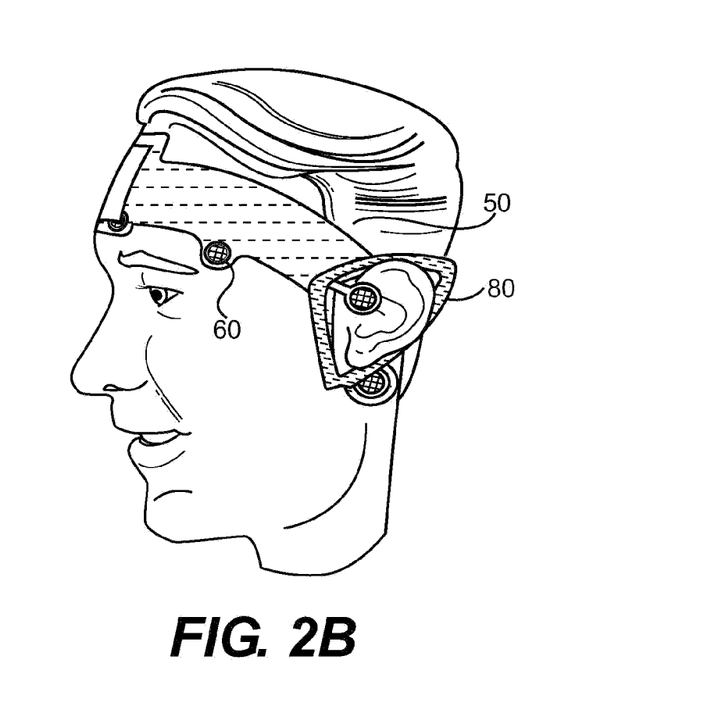
FIG. 2B illustrates the electrode set of FIG. 1B, as applied to a patient.
Figure 3:
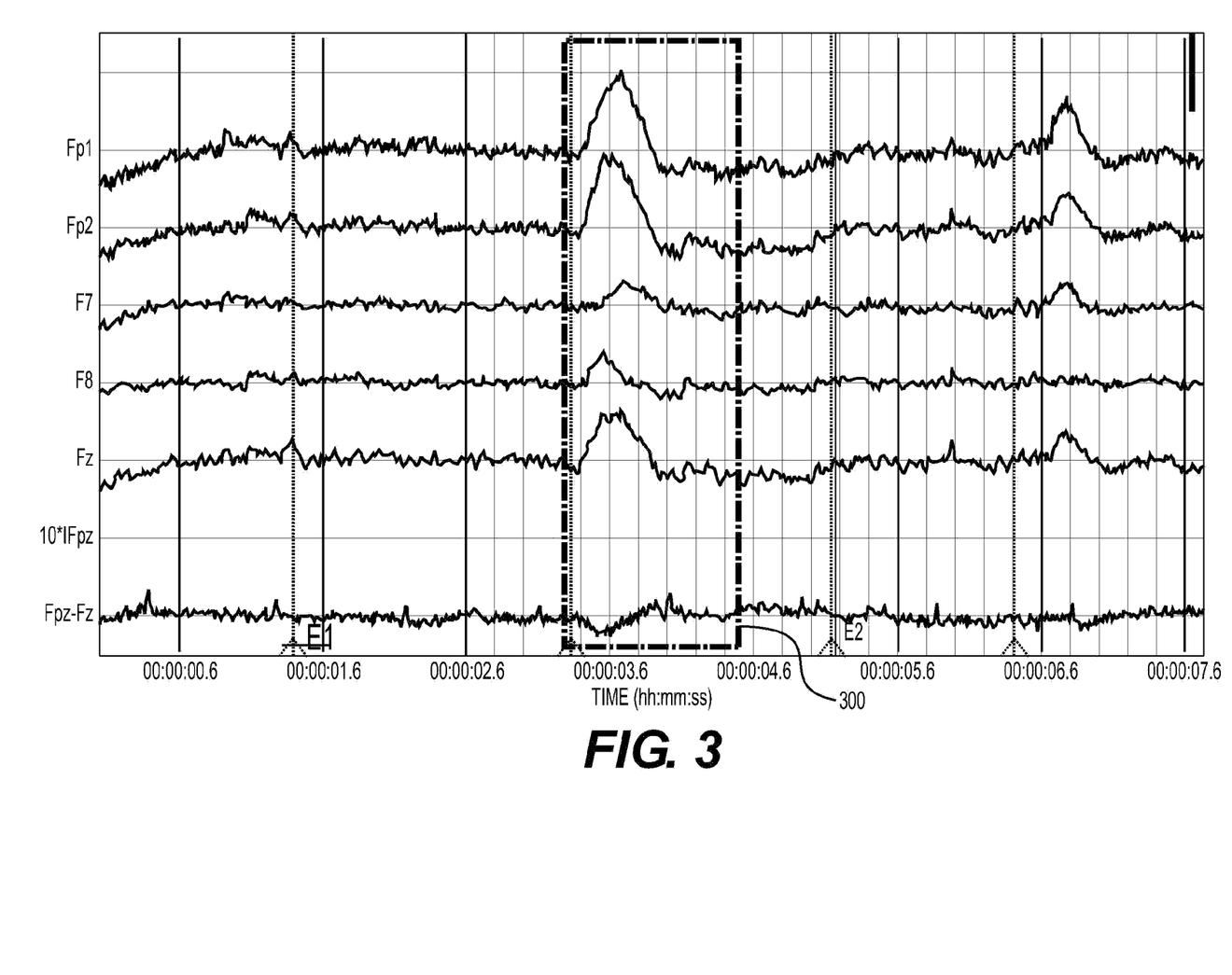
FIG. 3 shows approximately eight seconds of EEG that includes artifacts produced by vertical eye movements (VEM).
Figure 4:
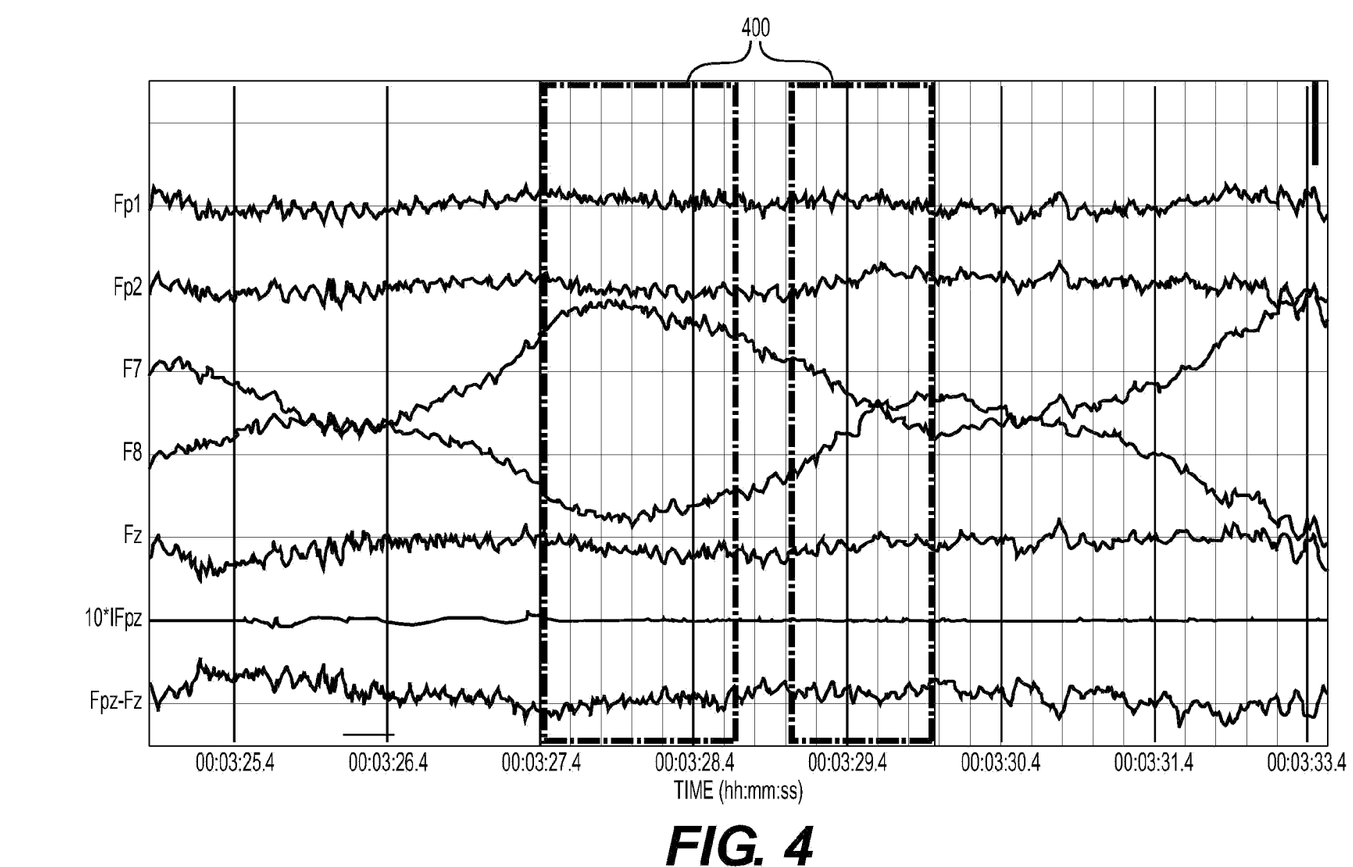
FIG. 4 shows approximately eight seconds of EEG that includes artifacts produced by horizontal eye movements (HEM).
Figure 5:
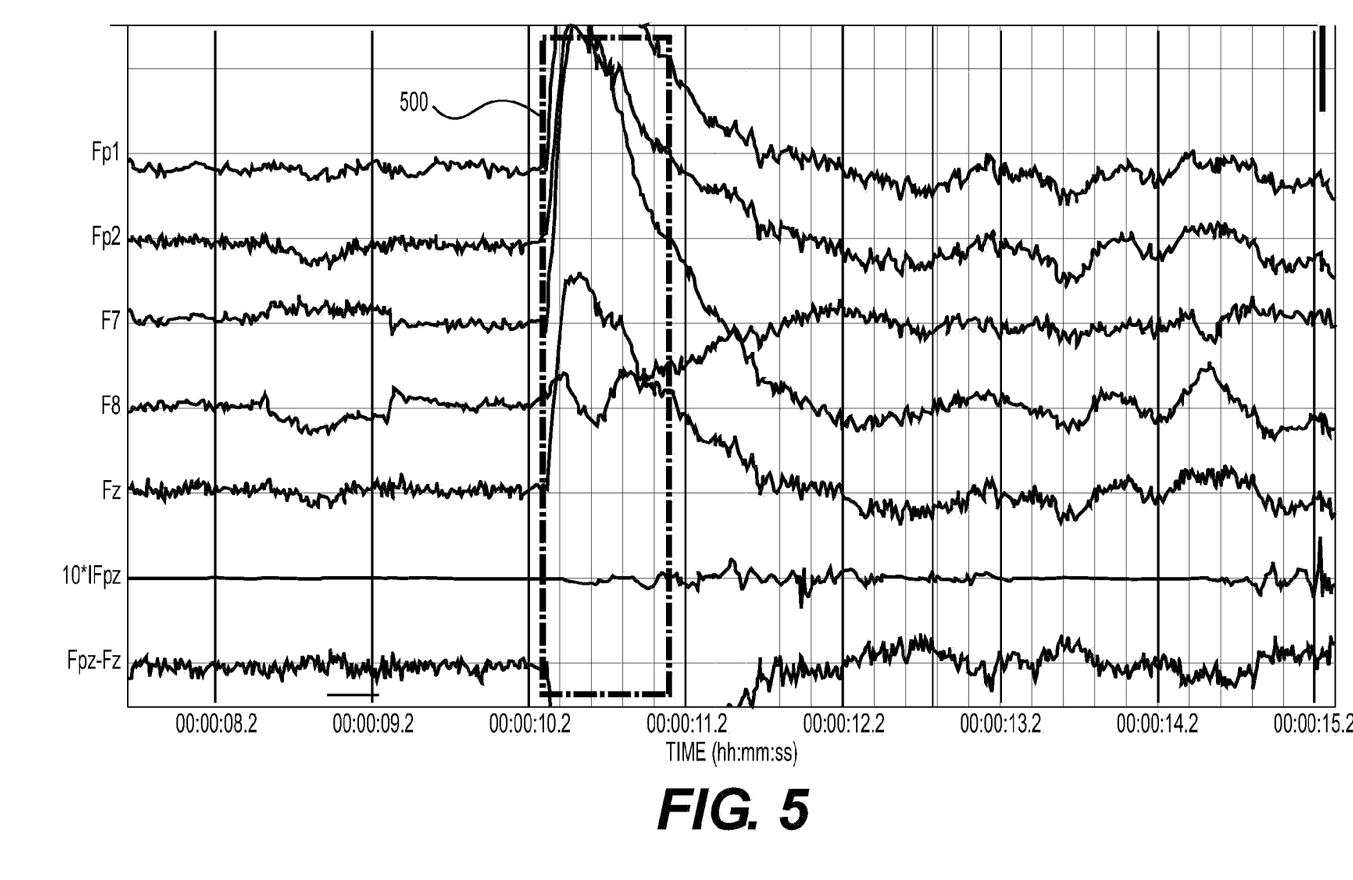
FIG. 5 shows approximately eight seconds of EEG that includes artifacts produced by cable/electrode movement (PCM).
Figure 6:
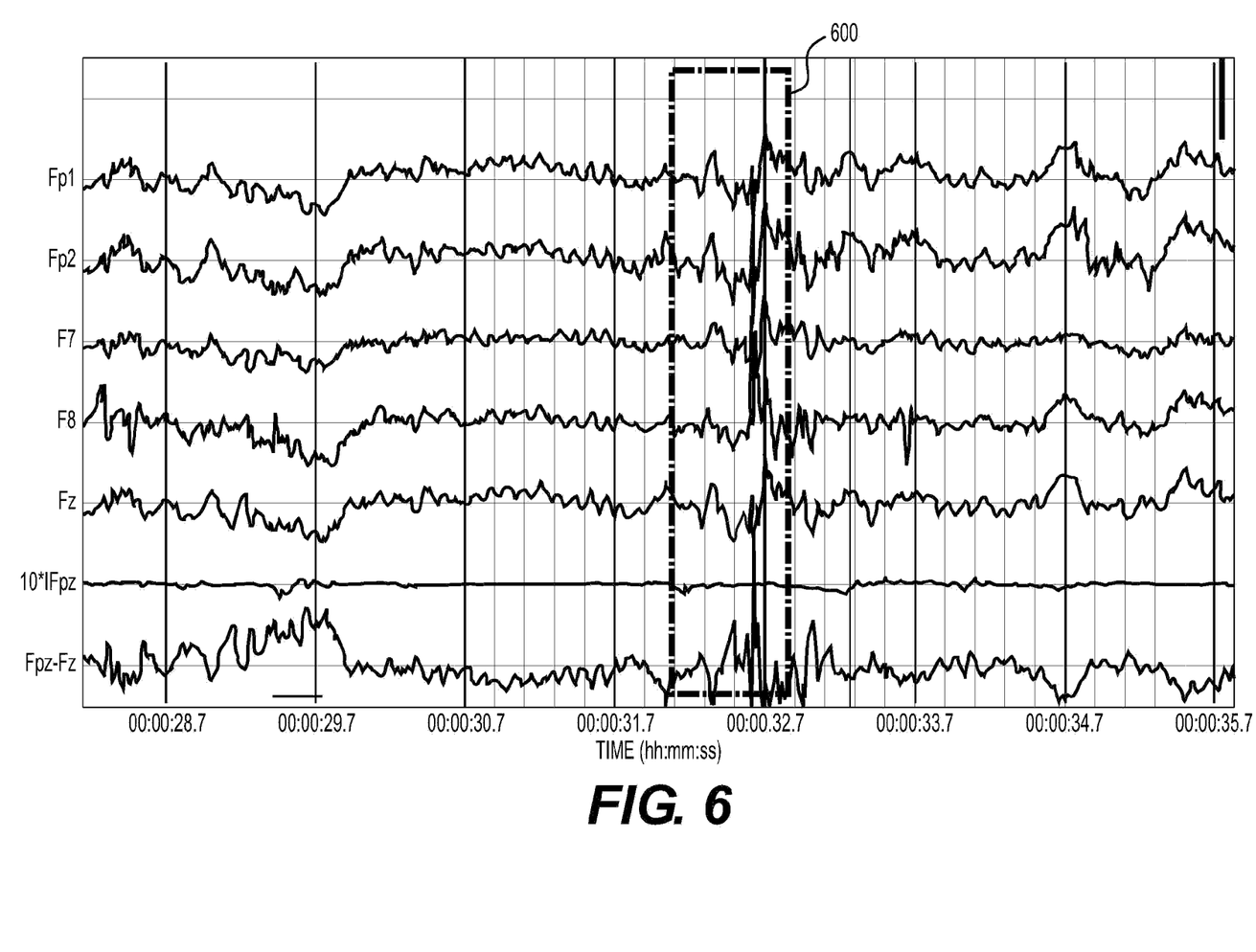
FIG. 6 shows approximately eight seconds of EEG that includes impulse artifacts (IMP).
Figure 7:
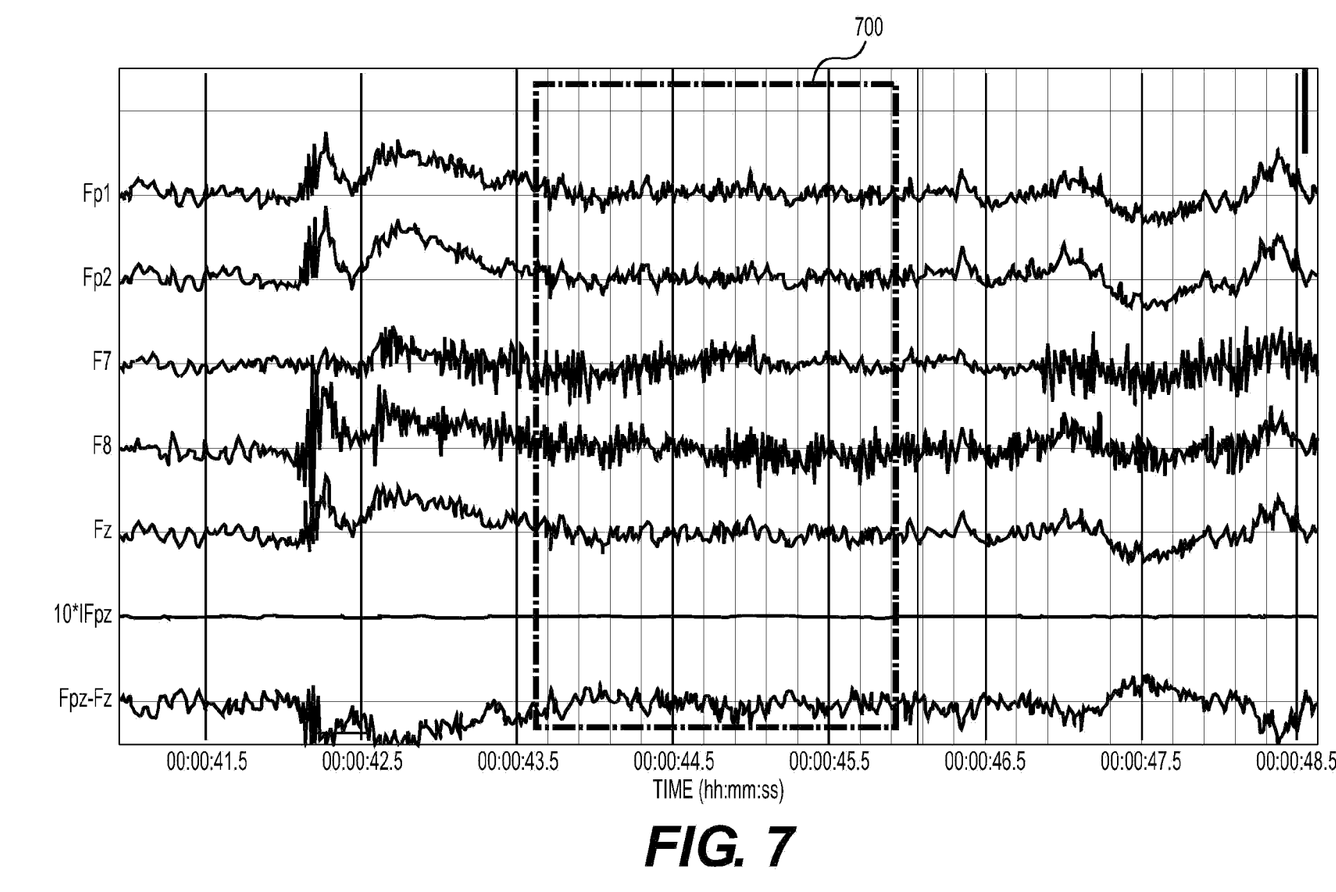
FIG. 7 shows approximately eight seconds of EEG that includes artifacts produced by muscle activity (EMG).
Figure 8:
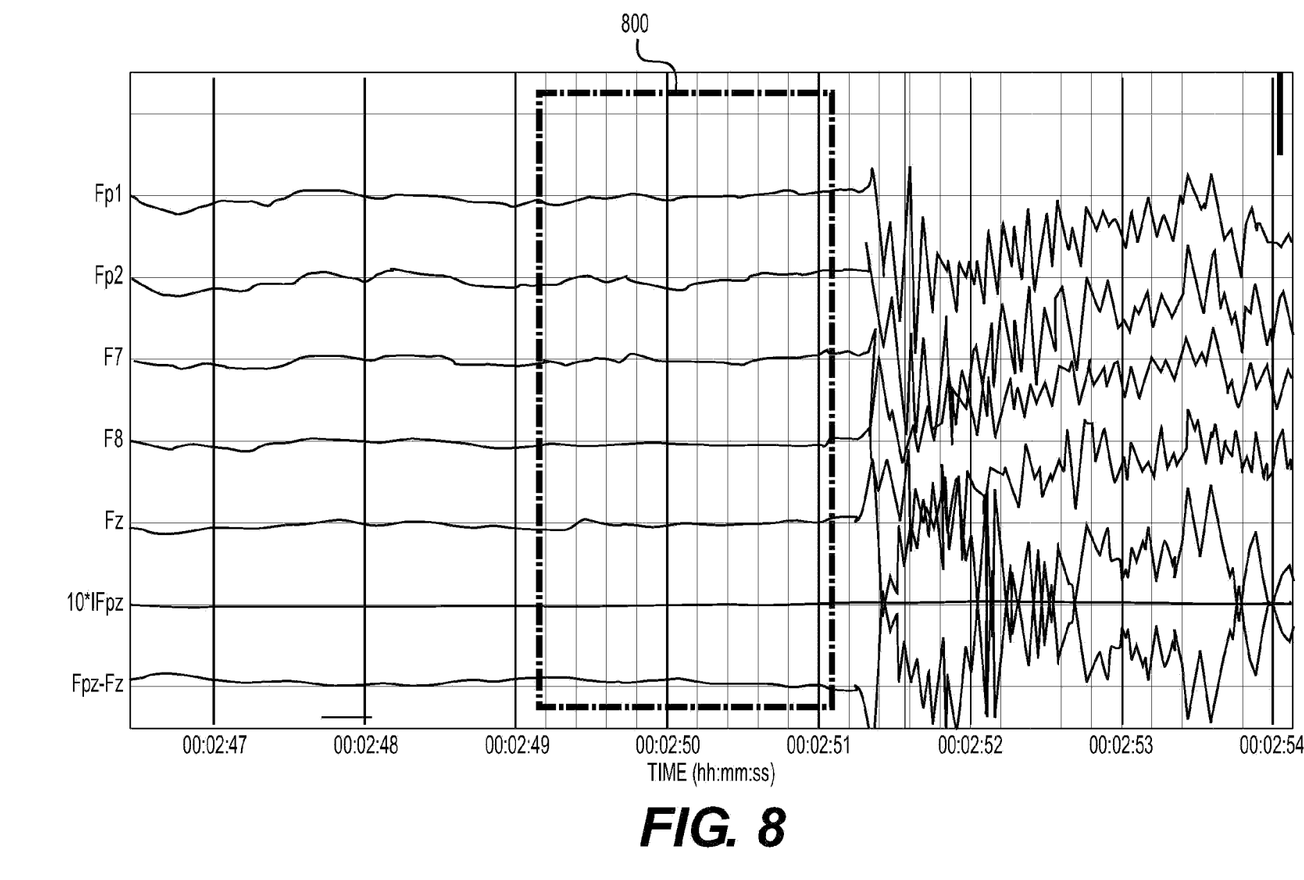
FIG. 8 shows approximately eight seconds of EEG that includes artifacts produced by significantly low-amplitude signal due to Burst Suppression (SLAS).

The circuitry 24 can include a number of circuitry types. For example the circuitry 24 can include processing circuitry configured to receive electrical signals from electrodes and to process such signal using filters (e.g., band pass, low pass, and/or high pass filters), as shown in FIGS. 2A-2B, and to convert such signals into data that can be further evaluated. In some embodiments, the circuitry can be configured to enable nonlinear processing, including nonlinear amplifiers. Further, the circuitry 24 can also include components configured to allow analysis of processed data and comparison of brain electrical activity data to normal data, or to previous or future measurements, as described in more detail below. Further, it will be understood that, although shown as a single component, multiple components can be included, either on a single chip or multiple chips.

The transmitter unit 26 can include a number of transmitter types. For example, the transmitter 26 may include a hardware connection for a cable or a telemetry system configured to transmit data to a more distant receiver 28, or a more powerful transmission system to redirect data to a database 32 that may be stored nearby or at a remote or distant location. In certain embodiments, the data can be transmitted and stored and/or evaluated at a location other than where it is collected.

The brain electrical monitoring system 10 may be configured to attach to various patient interfaces. For example, FIGS. 2A-2B illustrate an electrode set 50 for use with the system 10 of the present disclosure. As shown, the electrode set 50 includes one or more electrodes 60 for placement along the patient's forehead and mastoid region. As shown, the electrode set 50 includes a limited number of electrodes 60 to facilitate rapid and easily repeated placement of the electrodes 60 for efficient, but accurate, patient monitoring. Further, in one embodiment, the electrodes 60 may be positioned on a head band 70 that is configured for easy and/or rapid placement on a patient, as shown in FIG. 2B. Further, it will be understood that other electrode configurations may be selected, which may include fewer or more electrodes.

In certain embodiments, a limited frontal electrode montage can be used to implement the methods of the present disclosure, including at least two electrodes. In some embodiments, the at least two frontal EEG electrodes are positioned at FP1 and FP2 positions based on the expanded international 10/20 placement system. In some embodiments, the at least two frontal EEG electrodes are positioned at F7 and F8 positions based on the expanded international 10/20 placement system. In some embodiments, the electrodes include at least five electrodes positioned at FP1, FP2, F7, F8, and AFz positions based on the expanded international 10/20 placement system.

As noted, the electrode set 50 will be operably connected to the monitoring system 10. Generally, the electrodes 60 will be electrically coupled with the monitoring system 10 to allow signals received from the electrodes to be transmitted to the monitoring system 10. Such an electrical coupling will generally be through one or more electrical wires, but nonphysical connections may also be used.

To identify artifacts, EEG signals may be analyzed in certain temporal segments or epochs. Generally, the segment duration should be long enough to allow identification of artifacts in question, but as short as possible to minimize editing out segments or data that do not contain artifact. In some embodiments, segments having lengths between 10 to 500 ms are analyzed and/or edited out if they contain EEG artifacts. In one embodiment, the signals are analyzed in approximately 320 ms length segments or sub-epochs, although other signal lengths may be used depending, for example, on the type of brain electrical activity being analyzed. In certain embodiments, when editing out segments containing artifacts, data recorded just before and/or after the artifacts may also be edited out. For example, in some embodiments, segments of duration of 320 ms occurring immediately before and immediately after a segment containing artifact are automatically edited out.

In certain embodiments, slow lateral eye movements (HEMs) are identified, and brain electrical activity data segments containing lateral eye movement artifacts are edited out of the signal. In certain embodiments, HEM artifacts are identified as waveforms of 1 Hz or less that have opposite polarity at F7 and F8. Each of the two EEG channels F7 and F8 may band-pass filtered using an FIR filter with passband 0.5-3 Hz, producing signals F7f and F8f, the high-pass cut-off frequency of 0.5 Hz being chosen to ignore the influence of low-frequency activity occurring at frequencies below the delta_1 band (0.5-1.5 Hz). EEG segments containing HEM artifacts are identified wherever the difference signal F7f-F8f exceeds a threshold. In various embodiments, the threshold can be between 10 µV and 100 µV, or between 10 µV and 30 µV, or in one embodiment, approximately 24 µV.

In certain embodiments, vertical eye movement (VEM)/eye opening/eye closing (EOEC) artifacts are identified, and brain electrical activity data segments containing those artifacts are edited out of the signal. Detection of the electrophysiological effect of a vertical eye movement (VEM) (of which eye opening/closing is a sub-type) can performed by locating large excursions ("peaks") on the Fp1 and Fp2 leads. Since both eyes move in unison, only such excursions that occur concurrently and in the same direction (same polarity of the peaks) on Fp1 and Fp2 are identified as vertical eye movements. In some embodiments, each of the two signals Fp1 and Fp2 is first low-pass filtered in the range 0.5-5 Hz. In each segment, runs of samples exceeding a given threshold. In various embodiments, the threshold can be between 10 µV and 100 µV, or between 10 µV and 30 µV, or in one embodiment, approximately 24 µV. In each such run, the global extremum is located and its value is compared to average signal values on either side of it. If the absolute difference between the extremum and either average exceeds the threshold, the segment is identified as a candidate VEM artifact. After this processing has occurred on both leads, the results are combined to turn candidate VEMs to true VEMs wherever they occurred concurrently on Fp1 and Fp2 as described above. In certain embodiments, determining if temporal segments of the signal include artifacts due to eye movements includes filtering signals obtained from electrodes positioned at the Fp1 and Fp2 positions, comparing each signal to an average signal from the same electrode, determining if the signals exceed a threshold, and if the signal exceeds a threshold, determining if changes in the Fp1 and Fp2 signals occur concurrently, and if the changes do occur concurrently, identifying the segment as including artifacts.

In some embodiments, cable or electrode movement (PCM) artifacts, are identified, and brain electrical activity data segments containing those artifacts are edited out of the signal. In some embodiments, determining if temporal segments of the signal include artifacts due to cable or electrode movement includes identifying a signal amplitude greater than a threshold, and if any segment includes an amplitude greater than the threshold, identifying that segment as including cable or electrode movement artifacts. In certain embodiments, the threshold can be between 50 µV and 250 µV, or between 50 µV and 150 µV, or, in one embodiment, approximately 120 µV.

In some embodiments, impulse artifacts are identified, and brain electrical activity data segments containing those artifacts are edited out of the signal. In some embodiments, a frontal EEG channel is first high-pass filtered with cutoff frequency at to remove the alpha-1 band from the signal in that channel. In some embodiments, the cut-off frequency is 15 Hz. Next, high-frequency variations of signal amplitude in successive segments of 100 ms width with 50% overlap are examined. Within each segment, the value (max-min) is computed and trigger an IMP artifact detection when it exceeds a given threshold. In certain embodiments, the threshold can be between 25 µV and 250 µV, or between 50 µV and 125 µV, or in one embodiment, approximately 75 µV.

In some embodiments, muscle activity (EMG) artifacts are identified, and brain electrical activity data segments containing those artifacts are edited out of the signal. This artifact is characterized by high-frequency signals (above 20 Hz) occurring in bursts of variable duration. In certain embodiments, muscle movement artifacts are identified by band pass filtering a signal from at least one electrode in the range of the EEG $\beta 1$ band to produce signal E1 and band pass filtering the same signal in the range of the $\beta 2$ band to produce signal E2, and if relative energy of E2 relative to E1 exceeds a threshold, identifying the segment as containing muscle movement artifacts. In certain embodiments, the signal is band-pass filtered in the range of 25-35 Hz ($\beta 2$ band) and 15-25 Hz ($\beta 1$ band).

In some embodiments, brain electrical activity data segments containing significantly low amplitude signal (SLAS) are identified, and brain electrical activity data segments containing those artifacts are edited out of the signal. This artifact is meant to capture extremely low-amplitude EEG signals (at all frequencies) which occur, for example, when the brain is in Burst Suppression mode; a condition which can occur (but should be avoided) during anesthesia. No additional filtering of the signal is used for detection of this activity. In some embodiments, SLAS can be detected by looking for signal epochs with mean-square energy below a threshold. In certain embodiments, the threshold can be between 1 $\mu V^2$ and 25 $\mu V^2$, or between 10 $\mu V^2$ and 15 $\mu V^2$, or, in one embodiment, approximately 12 $\mu V^2$.

In some embodiments, brain electrical activity data segments containing atypical electrical activity pattern (AEAP) are identified, and brain electrical activity data segments containing those artifacts are edited out of the signal. This artifact includes unusual patterns of activity in the signal such as those that occur in the EEG of epileptic subjects during a convulsive or non-convulsive seizure. Such artifacts can be identified using a combination of wavelet analysis and fractal dimension computation, as described in A. Jacquin et al. "Automatic Identification of Spike-Wave Events and Non-Convulsive Seizures with a Reduced Set of Electrodes," *Proceedings of the* 29*th IEEE EMBS International Conference*, Lyon, France, August 2007.

The methods for automatically identifying and editing out brain electrical activity data segments that contain artifacts has been tested and validated by comparison to manual editing techniques. The process has been found to be suitable for editing recordings from patients with a variety of different pathologies, including, for example, traumatic brain injury with positive imaging, head injuries/concussions with negative or no imaging, subjects who had no head injury or evidence of CNS abnormalities, subjects with strokes or tumors, subjects with alcohol or drug encephalopathies, and other patient populations. In addition, the methods have been used to edit EEG recordings from patients with cerebro-vascular accidents (CVA) who frequently had the characteristic of frontal slow waves in their EEGs, indicating that the methods of the present disclosure remove pathology from the EEG by mistaking it as artifact.

Other embodiments will be apparent to those skilled in the art from consideration of the specification and practice of the devices and methods disclosed herein. It is intended that the specification and examples be considered as exemplary only, with a true scope being indicated by the following claims.

What is claimed is:

1. A method for automatically editing brain electrical activity data, comprising:
   obtaining a signal representing brain electrical activity from EEG electrodes on a patient;
   identifying artifacts in the signal due to lateral eye movement, wherein the signal includes two EEG channel signals corresponding to F7 and F8 electrode signals, and the identification comprises:
      determining that the F7 signal and the F8 signal have opposite polarities,
      filtering the F7 signal and F8 signal with a passband of 0.5 Hz-3 Hz, and
      determining whether a difference between the filtered signal F7 and the filtered signal F8 exceeds a predetermined threshold between 10 $\mu V$ and 100 $\mu V$; and
   generating an edited signal by removing segments of the signal that include the identified artifacts due to lateral eye movement.

2. The method of claim 1, further comprising identifying a significantly low amplitude signal due to burst suppression by identifying time segments of the signal from one of the EEG electrodes with a mean-square energy below a predetermined threshold, wherein the predetermined threshold is between 1 $\mu V^2$ and 25 $\mu V^2$.

3. The method of claim 1, further comprising;
   identifying artifacts due to cable or electrode movement, the identification comprising:
      identifying a signal amplitude greater than a predetermined threshold, wherein the predetermined threshold is between 50 $\mu V$ and 250 $\mu V$.

4. A method for automatically editing brain electrical activity data, comprising:
   obtaining a signal representing brain electrical activity from EEG electrodes on a patient;
   identifying signal artifacts due to vertical eye movement, wherein the signal includes two EEG channel signals corresponding to Fp1 and Fp2 electrode signals, and the identification comprises:
      low-pass filtering the Fp1 signal and the Fp2 signal at a cut-off frequency in the range of 0.5 Hz-5 Hz,
      identifying a global extremum in the filtered Fp1 signal and the filtered Fp2 signal,
      comparing the global extremum to average signal values on either side of the global extremum, for the filtered Fp1 signal and the filtered Fp2 signal,
      identifying candidate vertical eye movement artifacts when the difference between the global extremum and the average signal value of either side exceeds a predetermined threshold between 10 $\mu V$ and 100 $\mu V$, for the filtered Fp1 signal and the filtered Fp2 signal, and
      determining that candidate vertical eye movement artifacts are actual vertical eye movement artifacts when candidate vertical eye movement artifacts in the Fp1 signal and the Fp2 signal occur concurrently; and
   generating an edited signal by removing segments of the signal that include the identified artifacts due to vertical eye movement.

5. A method for automatically editing brain electrical activity data, comprising:
   obtaining a signal representing brain electrical activity from EEG electrodes on a patient;
   identifying impulse artifacts, the identification comprising:
      high-pass filtering the signal from one of the EEG electrodes to remove the alpha component of the signal with a cut-off frequency of 15 Hz, and
      determining whether a time segment of the signal includes amplitude variations greater than a predetermined threshold between 25 $\mu V$ and 250 $\mu V$;
   generating an edited signal by removing segments of the signal the signal that include the identified impulse artifacts.

6. A method for automatically editing brain electrical activity data, comprising:
   obtaining a signal representing brain electrical activity from EEG electrodes on a patient;
   identifying signal artifacts due to muscle activity, the identification comprising:
      band-pass filtering the signal from one of the EEG electrodes in the range of an EEG $\beta 1$ band to produce the signal E1 and band-pass filtering the same signal in the range of the $\beta 2$ band to produce signal E2, wherein the range of the $\beta 1$ band is 15 Hz-25 Hz and the range of the $\beta 2$ band is 25 Hz-35 Hz, and
      determining whether the energy of the signal E2 relative to the signal E1 exceeds a threshold; and
   generating an edited signal by removing segments of the signal that include the identified artifacts due to muscle activity.

7. A device for automatically editing brain electrical activity data, comprising:
   processing circuitry configured to perform operations, including:
      obtaining a signal representing brain electrical activity from EEG electrodes on a patient; and
      performing the following identification of artifacts in the signal:
         (a) identifying artifacts due to lateral eye movement, wherein the signal includes two EEG channel signals corresponding to F7 and F8 electrode signals, and the identification comprises:
            determining that the F7 signal and the F8 signal having opposite polarities,
            filtering the F7 signal and F8 signal with a passband of 0.5 Hz-3 Hz, and
            determining whether a difference between the filtered signal F7 and the filtered signal F8 exceeds a threshold;
         (b) identifying artifacts due to vertical eye movement, wherein the signal includes two EEG channel signals corresponding to Fp1 and Fp2 electrode signals, and the identification comprises:
            low-pass filtering the Fp1 signal and the Fp2 signal at a cut-off frequency in the range of 0.5 Hz-5 Hz,
            identifying a global extremum in the filtered Fp1 signal and the filtered Fp2 signal, comparing the global extremum to average signal values on either side of the global extremum, for the filtered Fp1 signal and the filtered Fp2 signal, identifying candidate vertical eye movement artifacts when the difference between the global extremum and the average signal value of either side exceeds a threshold, for the filtered Fp1 signal and the filtered Fp2 signal, and determining that candidate vertical eye movement artifacts are actual vertical eye movement artifacts when candidate vertical eye movement artifacts for Fp1 and Fp2 occur concurrently;

(c) identifying artifacts due to impulse artifacts, comprising:

high-pass filtering the signal from one of the EEG electrodes to remove the alpha component of the signal, and determining whether a time segment of the signal includes signal variations greater than a predetermined threshold;

(d) identifying artifacts due to muscle activity, comprising:

band-pass filtering the signal from one of the EEG electrodes in a range of an EEG $\beta1$ band to produce a signal E1 and band-pass filtering the same signal in a range of a $\beta2$ band to produce a signal E2, and determining whether an energy of the signal E2 relative to the signal E1 exceeds a threshold; and (e) identifying a significantly low amplitude signal due to burst suppression, comprising:

identifying time segments of the signal from one of the EEG electrodes with a mean-square energy below a predetermined threshold, wherein the predetermined threshold is between 1 $\mu V^2$ and 25 $\mu V$; and generating an artifact-free signal by removing segments of the signal that include the identified artifacts.

\* \* \* \* \*